US008506566B2

(12) United States Patent
Karidis et al.

(10) Patent No.: US 8,506,566 B2
(45) Date of Patent: Aug. 13, 2013

(54) ADJUSTABLE LENGTH STRUT APPARATUS FOR ORTHOPAEDIC APPLICATIONS

(76) Inventors: John Peter Karidis, Ossining, NY (US); Peter Morris Stevens, Salt Lake City, UT (US)

(*) Notice: Subject to any disclaimer, the term of this patent is extended or adjusted under 35 U.S.C. 154(b) by 1007 days.

(21) Appl. No.: 12/182,584

(22) Filed: Jul. 30, 2008

(65) Prior Publication Data
US 2009/0036892 A1   Feb. 5, 2009

Related U.S. Application Data

(60) Provisional application No. 60/962,540, filed on Jul. 30, 2007.

(51) Int. Cl.
*A61B 17/56* (2006.01)
(52) U.S. Cl.
USPC .......................................................... 606/57
(58) Field of Classification Search
USPC ............. 606/218, 233, 54–59, 258, 63, 68, 606/320, 326, 90, 105; 403/45, 109.4, 204
See application file for complete search history.

(56) References Cited

U.S. PATENT DOCUMENTS

| | | | |
|---|---|---|---|
| 3,473,528 A * | 10/1969 | Mishkin et al. | 606/54 |
| 4,536,114 A | 8/1985 | Belew | |
| 5,207,676 A * | 5/1993 | Canadell et al. | 606/54 |
| 5,601,551 A | 2/1997 | Taylor et al. | |
| 5,702,389 A | 12/1997 | Taylor et al. | |
| 5,891,143 A | 4/1999 | Taylor et al. | |
| 6,030,386 A | 2/2000 | Taylor et al. | |
| 6,383,156 B1 | 5/2002 | Enzerink et al. | |
| 6,537,275 B2 | 3/2003 | Venturini et al. | |
| 2002/0010465 A1 | 1/2002 | Koo et al. | |
| 2004/0059331 A1 * | 3/2004 | Mullaney | 606/59 |
| 2008/0039840 A1 * | 2/2008 | Songer et al. | 606/61 |

FOREIGN PATENT DOCUMENTS
WO    WO03086212    10/2003

OTHER PUBLICATIONS

International Search Report and the Written Opinion of the International Searching Authority, International Application No. PCT/US2008/061756, dated Sep. 19, 2008.
International Search Report and the Written Opinion of the International Searching Authority, International Application No. PCT/US2008/071604, dated Feb. 4, 2009.
International Search Report and the Written Opinion of the International Searching Authority, International Application No. PCT/US2008/071671, dated Feb. 19, 2009.

(Continued)

*Primary Examiner* — Pedro Philogene
*Assistant Examiner* — David Comstock
(74) *Attorney, Agent, or Firm* — Myers Wolin, LLC

(57) ABSTRACT

An adjustable-length orthopaedic strut apparatus having minimal x-ray absorption, the capability to produce small length adjustments with minimal axial backlash, and a body devoid of exposed threads, the apparatus having an outer telescoping strut element, an inner telescoping strut element, a threaded drive element rotationally mounted inside the outer telescoping strut element and engaging threads inside the inner telescoping strut element, and an input gear-train arranged to produce fine adjustment of the strut length by generating rotation of the threaded drive element that can be smaller than the input gear rotation. A preferred embodiment also includes compliant preload structures for reducing axial backlash between all moving elements, and one or more locking pins which can be selectively disengaged to adjust the compressive stiffness of the adjustable length strut.

3 Claims, 5 Drawing Sheets

(56) References Cited

OTHER PUBLICATIONS

URL: http://global.smith-nephew.com/us/TAYLOR_SPATIAL_FRAME_7441.html Retrieved: Mar. 10, 2009.
URL: http://global.smith-nephew.com/us/ILIZAROV_EXTERNAL_FXR_OVW_13957.html Retrieved Mar. 10, 2009.
URL: http://www.orthofix.com/products/sheffield.asp Retrieved Mar. 10, 2009.
URL: http://global.smith-nephew.com/us/JET_X_BAR_UNILATERAL_FIX_7243.html Retrieved Mar. 10, 2009.
URL: http://www.orthofix.com/products/xcaliber_fixator2.asp Retrieved Mar. 10, 2009.
URL: http://www.jcharlestaylor.com/spat/01Correction.html Retrieved Mar. 10, 2009.

* cited by examiner

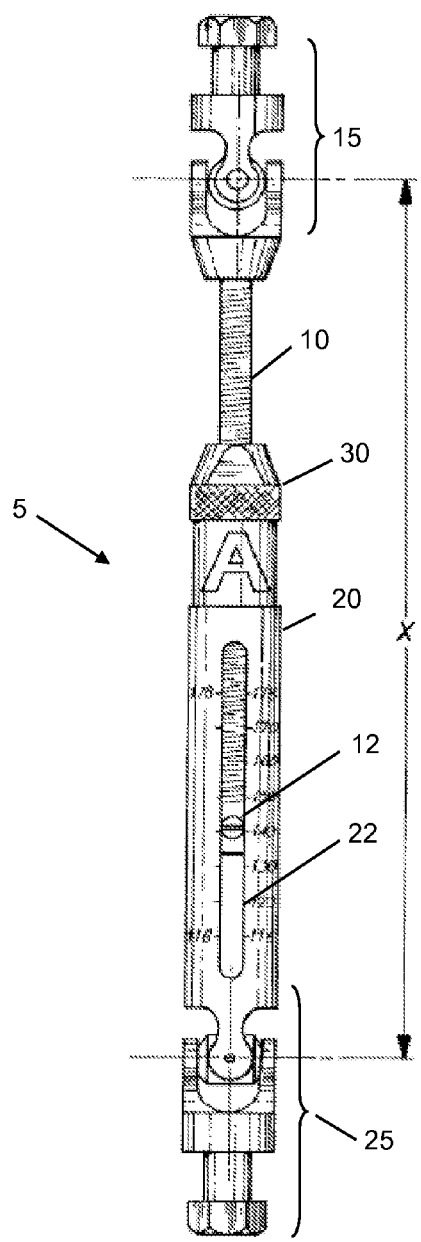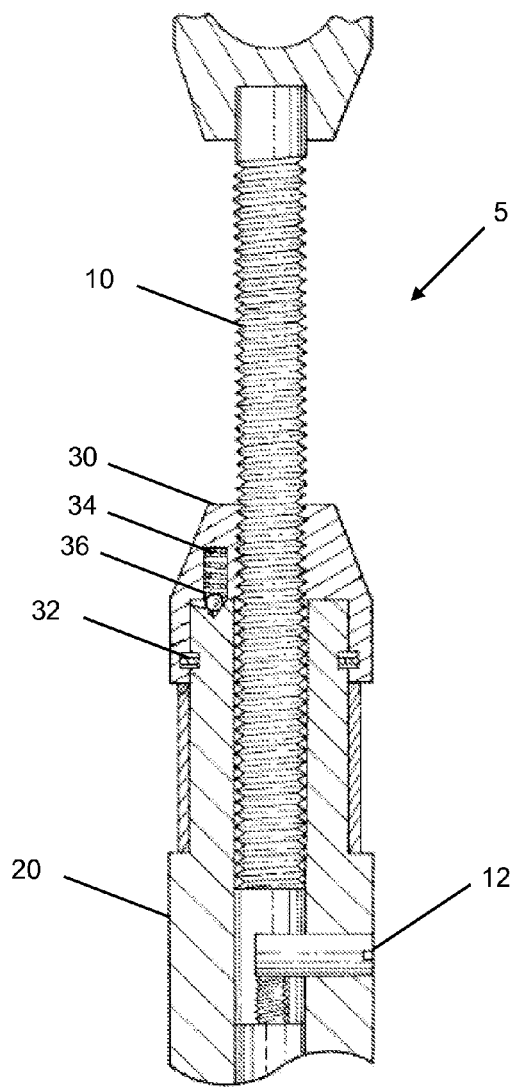
Fig. 1A
Prior Art
Fig. 1B
Prior Art

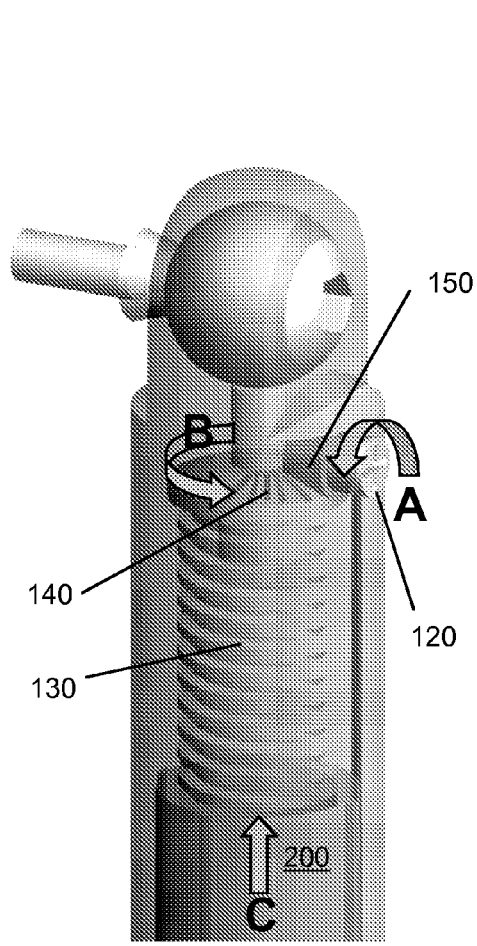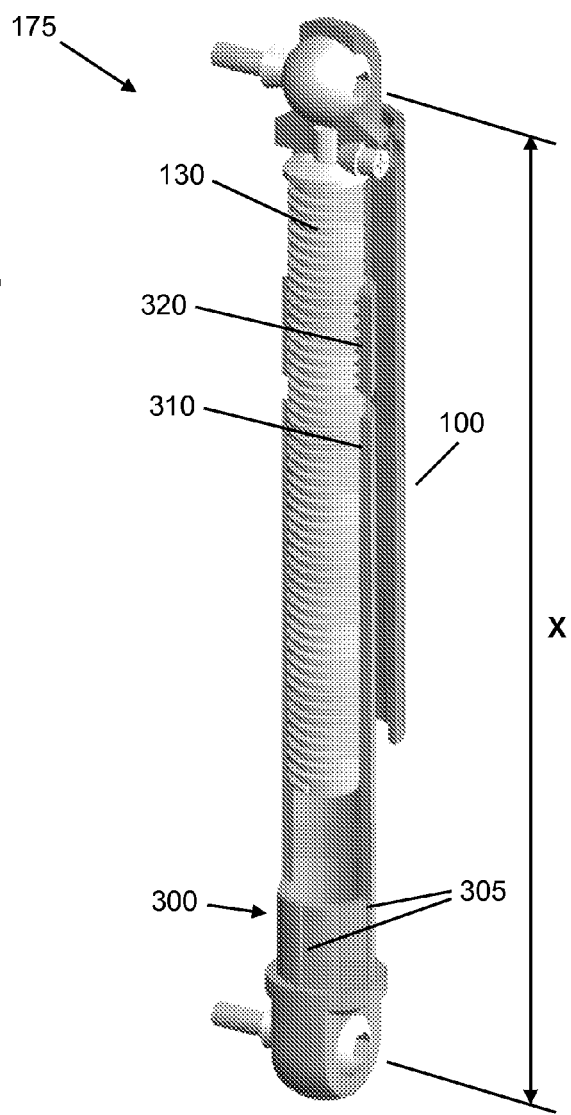
Fig. 4
Fig. 5

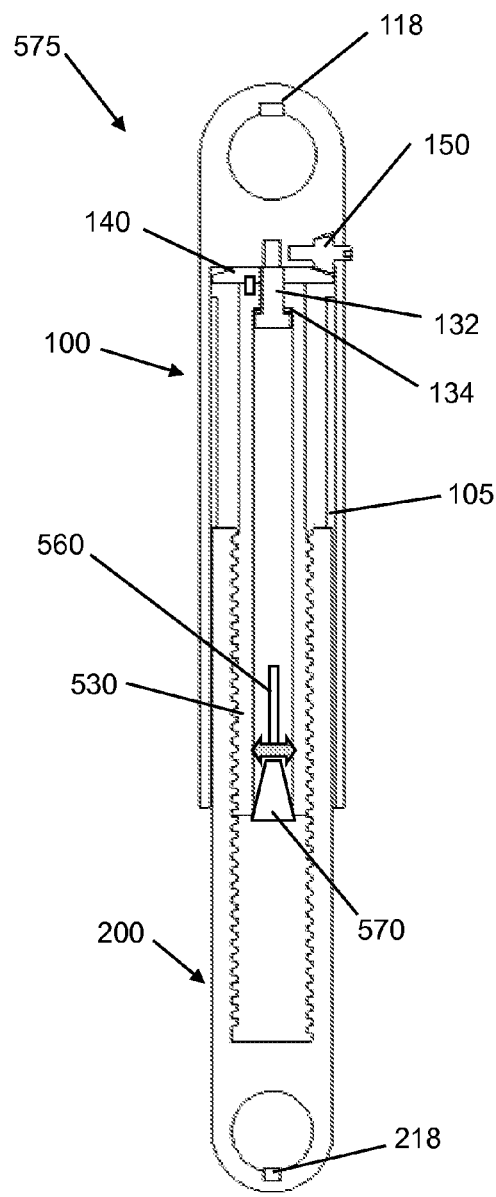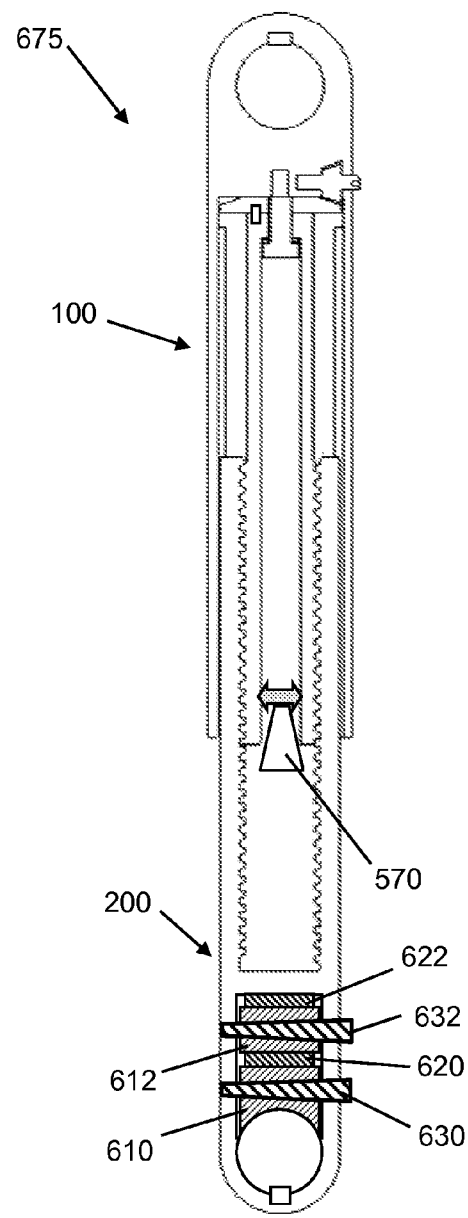
Fig. 8
Fig. 9

ADJUSTABLE LENGTH STRUT APPARATUS FOR ORTHOPAEDIC APPLICATIONS

CROSS REFERENCE TO RELATED APPLICATIONS

This application claims the benefit of U.S. Application 60/962,540, filed Jul. 30, 2007, the contents of which are expressly incorporated herein by reference.

FIELD OF THE INVENTION

This invention relates generally to the field of adjustable length struts and more specifically to adjustable length strut apparatus for external orthopaedic fixator applications.

BACKGROUND

External orthopaedic fixators are used to position two or more bone elements relative to one another, in either a fixed or an adjustable position, and often use one or more adjustable length struts to define the relative location of the two separate bone segments.

One example of a highly adjustable external fixation device is the Taylor Spatial Frame sold by Smith & Nephew (http://global.smith-nephew.com/us/TAYLOR_SPATIAL_FRAME__7441.htm) which uses 6 adjustable-length struts mounted between two circular frames (in a configuration known to the robotics community as a "Stewart platform") to provide full 6-degree-of-freedom (DOF) positioning capability. The struts in this example use metal threaded rods extending from a metal tubular structure, with a threaded ring rotatably captured on the end of the tubular structure defining the adjustable axial extension of the threaded rod. The design of the threaded ring provides a mechanical detent allowing a repeatable adjustment of one full revolution of the ring, with a full revolution typically corresponding to an axial extension of 1 mm.

Another example of an adjustable frame, this time of the Ilizarov type, is also provided by Smith & Nephew (http://global.smith-nephew.com/us/deformitycorrection/ILIZAROV_EXTERNAL_FXR_OVW__13957.htm). In this design, the frame is not capable of full 6-DOF positioning, but instead uses 3 or 4 extendable struts which are rigidly mounted to at least one circular frame, and which provide control of the axial displacement and 2 tilt angles of a second frame relative to the first frame. This particular design also uses a metal threaded rod extending from a metal tubular structure, but in this case the rotating threaded ring is adapted with a spring loaded latch lever which engages with detents to enable repeatable adjustment in increments of ¼ revolution.

Another example of a partially adjustable external fixator is the Sheffield Ring Fixator from Orthofix (http://www.orthofix.com/products/sheffield.asp).

Yet another type of external strut, generally called a unilateral fixator, uses a single adjustable-length strut to define the position of two swiveling mounting brackets, each of which holds half-pins which engage bone segments. Examples of this type of strut include the Jet-X unilateral fixator from Smith & Nephew (http://global.smith-nephew.com/us/deformitycorrection/JET_X_BAR_UNI-LATERAL_FIX__7243.htm) and the XCaliber Articulated Ankle Fixator from Orthofix (http://www.orthofix.com/products/xcaliber_fixator2.asp). Both of these systems use molded plastic body elements constructed from radiolucent fiber-reinforced polymer materials to provide a slidably adjustable structure. Both of these systems also use a radio-opaque metal bolt or similar element to clamp the sliding elements together to define a fixed length.

Existing adjustable length struts for orthopaedic applications suffer from several deficiencies. The struts used in the Taylor Spatial Frame provide a manually operable input ring for adjusting length, but this design provides little security against accidental rotation (e.g., as a result of an object brushing up against the strut), and provides no ability to prevent unwanted adjustment by, for example, curious or fidgety child patients. Furthermore, there is no way to provide a reliable adjustment of less than one full turn, or less than one full millimeter of length adjustment. Other disadvantages of this design include the presence of exposed threads which can gather dirt, and the relatively large weight and radio-opaque characteristics of the all-metal struts.

The struts used in the Smith&Nephew Ilizarov frame do provide for ¼ turn increments, but the structure used to provide this capability adds quite substantially to the weight of the strut. Furthermore, there is still no means for preventing undesired manual adjustment; the threaded rods are still exposed in the same manner as the struts in the Taylor Spatial Frame; and the all-metal design strongly absorbs X-rays used to image the bone locations.

All of the above struts also suffer from axial backlash, which limits the precision and stiffness with which the two bone segments can be held in position. This unavoidable backlash is caused by manufacturing clearances between the threaded rod and the threaded adjuster elements, and in the rotational mounting of the adjuster to the outer tube structure. While these clearances are each generally small (well under 1 mm) the combination of several clearances can result in total backlash that is a significant fraction a millimeter, or more, and which can potentially have an adverse effect on bone healing.

The slidable polymer struts used in the XCaliber and Jet-X products are mostly radiolucent, but they still require a metal locking element somewhere near the mid-point of the strut length, and this metal element can still obscure X-ray images in inconvenient locations. The manual clamping design of these struts does eliminate backlash but the length adjustment of these devices is not simple, and generally cannot be done safely by the patient.

SUMMARY

An adjustable-length orthopaedic strut is provided that enables precise length adjustments which can be significantly smaller than the typical daily adjustment increment of 1 mm, but that is also resistant to accidental length adjustment. In accordance with one embodiment, there is disclosed a strut apparatus comprising: an outer telescoping strut element, an inner telescoping strut element, means for preventing significant rotation of the outer telescoping strut element relative to the inner telescoping strut element, a threaded drive element rotationally mounted inside the outer telescoping strut element, and means to enable rotation of the threaded drive element relative to the outer telescoping strut element; wherein the threaded drive element rotation causes axial motion of the inner telescoping strut element relative to the outer telescoping strut element. Also in accordance with an embodiment of the invention, the outer telescoping strut element has a first end joint and the inner telescoping strut element has a second end joint, wherein both end joints are adapted to allow at least partial rotation around at least two orthogonal axes.

In accordance with a preferred embodiment, the drive element is coarsely threaded, typically having a thread pitch greater than 1 mm and thus producing more than 1 mm of axial motion when rotated one full revolution, and the means to enable rotation of the threaded drive element comprises an output gear rotatably fixed to the coarsely threaded drive element and an input gear adapted for external adjustment, wherein one rotation of the input gear produces less than one rotation of the output gear and the coarsely threaded drive element.

One advantage of the preferred embodiment is that a lightweight, low-cost, and largely radiolucent orthopaedic strut can be conveniently manufactured wherein the telescoping inner and outer strut elements and the coarsely threaded drive element are molded out of optically opaque, translucent, transparent, or color-tinted plastic. Preferably, the telescoping strut elements and the means for adjusting the length of the adjustable length strut apparatus form a substantially radiolucent central portion extending in both directions from a mid-point equidistant between the end joints, and extending the majority of the distance from the mid-point to the first end joint or the second end joint. The substantially radiolucent central portion can be comprised of relatively thick sections of radio-transparent materials such as but not limited to plastic, as disclosed above, but can also be comprised of very thin sections of radio-opaque materials such as but not limited to metal.

Also provided are means to improve the positioning precision of the adjustable length orthopaedic strut by internally preloading locations having mechanical clearance, so as to minimize significant sources of axial backlash. In one embodiment, the axial backlash between the threaded drive element and the internally threaded strut element is minimized by segmenting and expanding a portion of the internally threaded drive element so as to remove radial and axial thread clearance. The axial clearance at the rotating joint between the threaded drive element and the outer telescoping element is minimized by axially preloading the rotatable joint with a spring washer or other compliant element for example. And in a further embodiment, mechanical clearances between a spherical end-joint on each strut element and the body of the strut element are also minimized through the use of elastic preloading elements. Lastly, in yet another embodiment, the stiffness of the strut in response to compressive axial loading can be easily reduced (e.g., to allow more load-sharing by the healing bone prior to removal of the fixator) by removing or otherwise disengaging one or more locking pins that fix the position of one or more rigid elements which are stacked on top of elastic elements and which together act to limit the axial motion of at least one of the spherical end-joints.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 1A is an elevation view of a Prior Art adjustable length strut.

FIG. 1B is a cross sectional view of a portion of the Prior Art adjustable length strut of FIG. 1A.

FIG. 4 is a magnified, partially transparent view of an adjustment mechanism of the strut of FIG. 2.

FIG. 5 is a partially cut-away view of another embodiment of a strut of the present invention adapted for unidirectional action.

FIG. 8 is a section view of an embodiment of the invention illustrating preloading for elimination of backlash.

FIG. 9 is a section view of an embodiment of the invention illustrating preloading for elimination of backlash and adjustability of compressive stiffness.

DETAILED DESCRIPTION OF THE PREFERRED EMBODIMENTS

Figure 2:
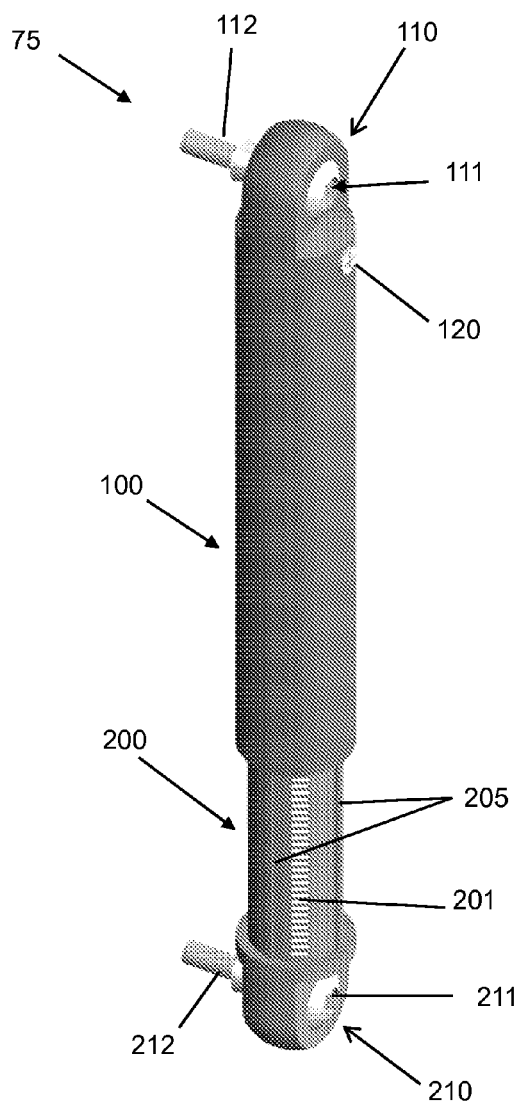
FIG. 2 is a perspective view of one embodiment of an adjustable length strut of the present invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

FIG. 1A shows an example of a prior art strut 5 primarily comprising an exposed threaded metal rod 10, which telescopes out of a metal tube structure 20. A threaded adjustment ring 30 is rotatably mounted to the end of the metal tube 20 and engages with the threads on the threaded rod 10. A multi-axis pivot 15 is attached to the threaded rod 10, and another multi-axis pivot 25 is built into the end of the metal tube 20. The threaded rod 10 has an extension pin 12 which rides in slot 22 formed in the tube 20 in order to prevent rotation of the rod 10 relative to the tube 20.

FIG. 1B shows a sectional view of the axial adjustment region of the same prior art strut 5. This view illustrates that the internally threaded adjustment ring 30 engages with the externally threaded rod 10, and is rotatably attached to the end of the tube 20 using a retaining ring 32. Also shown is a mechanical detent mechanism comprising a small spring 34 and a ball 36 which fits into a small depression formed on the end face of the tube 20.

As can be seen from these figures, this prior art strut 5 has exposed threads on the outside of the structure which can collect dirt. While the adjustment ring 30 is adapted to be easily adjusted in increments of one full turn, the ring can also be easily rotated by accident. This design also has unavoidable clearances in the mating threads between the ring 30 and the rod 10, and between the retaining ring 32 and both the tube 20 and the ring 30. Additional clearances are present between individual moving elements in the multi-axis pivots 15 and 25. All of these clearances together produce backlash (also known in the art as "slack" or "lost motion") that limits the precision with which the axial length of the strut can be adjusted, because it creates a region of very low stiffness around the desired adjustment length. Changes to the length of the strut in response to external forces can occur with little or no resisting force until the all of the clearances are compressed and solid contact is established between all mating pairs of elements.

FIG. 2 shows the exterior of one embodiment of a strut 75 comprising an outer telescoping strut element 100 with a multi-axis "rod-end" type of joint 110 at one end, and an inner telescoping strut element 200 with multi-axis end-joint 210 at an opposite end. The joints 110 and 210 contain threaded mounting studs 112 and 212 having a partially spherical portion, each with a socket head indentation 111 and 211 or similar feature to enable convenient mounting of the studs to a circular frame or other fixator element (not shown). The inner telescoping strut element 200 slides inside of the outer telescoping element 100, while axial ridges 205 on the outside of the inner telescoping element 200 engage with mating features on the inside of the outer telescoping element 100 to prevent rotation of the inner telescoping strut element 200 relative to the outer telescoping strut 100. A visual length indicating scale 201 can be etched, engraved, molded, printed or attached onto the inner telescoping element 200 in order to provide a visual indication of the total length of the adjustable strut assembly. Other methods of providing such a scale 201 are contemplated. Adjustment of the strut length is accomplished by rotation of adjusting element 120, (shown in this embodiment as having the form of a Phillips-type screw head) which rotates within the outer telescoping tube 100. As can be seen in FIG. 2, there are no exposed threads in this embodiment, only generally smooth external surfaces which will be unlikely to collect dirt or grime. Any small ridges or discontinuities that remain, such as the axial ridges 205 or ridges that may be present in this illustrative example, can easily be designed to minimize the potential for capture of dirt or debris.

It will be appreciated that the geometry of the adjusting element 120 is not limited to a Phillips head screw, but could also take any form of hand-operated knob or crank, or any one of a variety of fittings for rotation by any tool, including but not limited to a socket head (for use with an Allen wrench), a hex head, a Torx drive socket, a cylindrical lock feature, or any other geometry, without departing from the scope of the invention. Those skilled in the art will also appreciate that the rod-end mounting features 110 and 210 need not be mounted orthogonally to the axis of the strut, and can be replaced with any type of single-axis or multi-axis joint, or even a rigid non-pivoting connection where desired, without departing from the scope of the invention.

Figure 3:
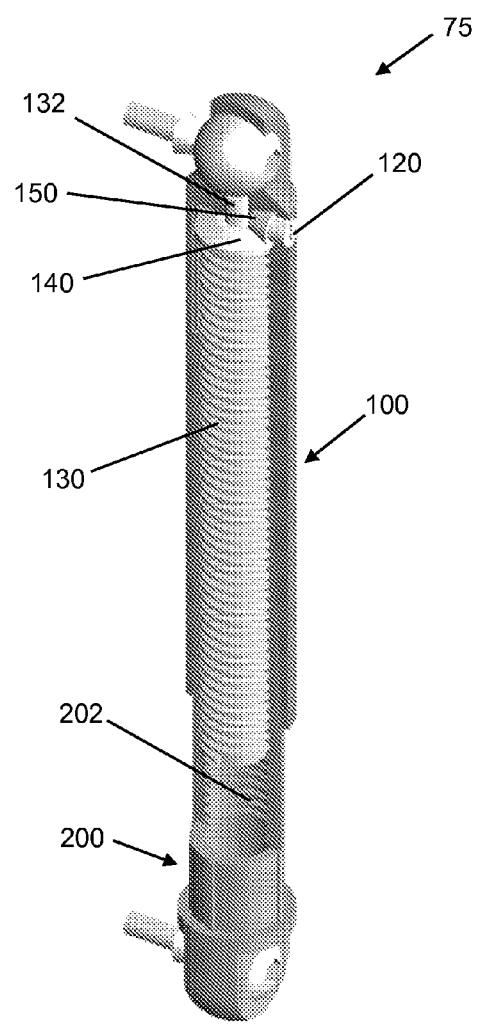
FIG. 3 is a partially cut-away view of FIG. 2.

FIG. 3 shows a partial cut-away view of the strut shown in FIG. 2 and illustrates a rotating threaded drive element 130 which is rotatably attached inside the outer telescoping tube 100 and which engages with threads 202 on the inside surface of the inner telescoping tube 200. The drive element 130 can be a hollow tube with a smaller diameter aperture at the end, and in this case the rotatable connection can be made using a shoulder screw 132 or other similar means which allows the threaded drive element 130 to rotate inside the outer telescoping tube 100 without translating substantially in the axial direction. If the drive element 130 is solid, the rotatable connection can be made using a smaller diameter extension of the drive element and a mating nut or other fastener, or using any other means which are known to those skilled in the art. A first bevel gear 140 (gear teeth not shown) is attached to, and rotates with, the threaded drive element 130. The first bevel gear 140 mates with a second bevel gear 150 (gear teeth not shown) which is mounted inside the outer telescoping strut 100. The adjusting element 120 is attached to, or built into, the second bevel gear 150 such that rotation of the adjusting element 120 about an axis generally orthogonal to the axis of the adjustable strut causes rotation of the second bevel gear 150, which in turn causes rotation of the first bevel gear 140 and the attached threaded drive element 130 about the longitudinal axis of the adjustable strut assembly 75.

In a preferred embodiment, the outer telescoping strut 100, the inner telescoping strut 200, and the threaded drive element 130 are all fabricated from a radiolucent material. An example of such fabrication is the molding of polymer material with the possible addition of reinforcing fibers also made of radiolucent material. In this manner, even if any of the bevel gears 140 and 150, the shoulder screw 132, or rod-end elements 112 or 212, are made of metal or other radio-opaque material, the main central portion of the strut assembly, which is the area most likely to obscure the healing bone region of orthopaedic interest, would be radiolucent. This radiolucent region can be seen to extend from the strut mid-point (defined here as the point equidistant from the two rod-ends) in both directions for the majority of the distance from the mid-point to the rod-end joints. Thus, the assembled strut is radiolucent over at least the central half of the region between the rod-ends.

In one embodiment, the threaded drive element 130 and inner telescoping element 200 with matching threads could be made of metal with relatively fine-pitch threads (on the order of 1 mm pitch). In another embodiment, it may be desirable to mold the parts out of a polymer material which may not have the strength or precision to enable the use of fine threads. In a molded embodiment, the threads may have a larger pitch (perhaps 2 mm or more) than the desired daily adjustment increment of approximately 1 mm. Therefore, it is desirable to provide a reliable means for making adjustments of significantly less than 1 full revolution of the threaded drive element 130. In a preferred embodiment, this is achieved by choosing the "input" or second bevel gear 150 to have significantly fewer teeth than the first bevel gear 140 which is mounted to threaded drive element 130. In this manner, the angular rotation of the threaded drive element 130 is substantially less than the angular rotation of the input gear 150.

This is illustrated more clearly in FIG. 4, which shows an enlarged, partially transparent view of a portion of the adjustable strut 75 in FIG. 3. In this non-limiting example, the threads on the threaded drive element 130, and the mating threads on the inside of inner telescoping strut element 200 have a pitch of 2 mm. The input bevel gear 150 is sized to contain one-half as many teeth as the first bevel gear 140. Thus, one revolution (arrow A) of the input bevel gear 150 (via the adjustment feature 120) produces only one half of a revolution (arrow B) of the bevel gear 140 and threaded drive element 130, which in turn produces 1 mm of axial displacement (arrow C; corresponding to ½ of the thread pitch) of the inner telescoping tube 200. Similarly, a one-quarter turn rotation of the adjuster element 120 (which would be conveniently indicated by the four-spoke pattern of a standard Phillips head screw) produces a one-quarter millimeter change in the overall strut length. Of course, other gear ratios and gear configurations can be substituted without departing from the scope of the invention. With a reasonable amount of gear reduction, a reasonably fine thread pitch on the threaded drive element 130, and markings (not shown) to indicate small fractional-rotation inputs to the adjustment element 120, length-adjustment increments of ⅒ mm or less could be achieved.

Many orthopaedic procedures for gradual bone lengthening or repositioning implement a program of length changes having an average rate of approximately 1 mm per day. However, a single 1 mm increment performed once per day represents a fairly large and instantaneous repositioning of the healing bone. It is believed that a more gradual adjustment, such as four adjustments of ¼ mm per day for example, would be easier for the healing bone to tolerate. Thus, the ability to easily and consistently implement adjustments of ¼ mm or less, or to divide out a single day adjustment into multiple partial-day adjustments, is an important capability. The use of a gear reduction system enables small axial displacement increments to be made even if the thread pitch is relatively large, as might be necessary to provide acceptable strength or tolerances in a strut constructed with molded polymer parts.

FIG. 5 shows an alternative embodiment of a strut 175, which is adapted to act as a preloading strut that is designed to define a minimum length and to be able to impart force in the lengthening direction, but designed so as to not restrict the strut from extending to be longer than the adjusted minimum length. In this embodiment, the telescoping portion of the inner telescoping strut element 200 with internal threads 202 of FIG. 3 has been replaced by inner telescoping element 300, which is sub-divided into an unthreaded portion 310 and a short threaded portion 320. Both portions 310, 320 have axial ridges or other features 305, for example, which mate with corresponding grooves or other features on the inside of the outer telescoping strut element 100 to prevent rotation of both the threaded portion 320 and the unthreaded portion 310 relative to the outer telescoping strut element 100. As will be apparent to those skilled in the art, rotation of the inner threaded drive element 130 will cause translation (without rotation) of the threaded portion 320, and this threaded portion 320 will define a minimum overall strut length X. Rotation of the drive element 130 can thus generate forces in the "lengthening" direction, but will not exert any "retracting" force on the inner telescoping strut element 300. It should be noted that a portion of the outer telescoping element 100 in FIG. 5 has been shown detached and shifted away from the unthreaded and threaded portions 310 and 320 for purposes of clarity only, and does not represent the operational orientation of the elements, where the outer telescoping element 100 would be closely fitted around the inner telescoping elements 310 and 320, with mating axial features engaged to prevent relative rotation.

In some orthopaedic applications, it is important that the strut be capable of withstanding very large forces. In these cases, such as leg reconstruction of large adult patients, it may be preferable for the outer telescoping strut element 100, the inner telescoping strut element 200, 300, and the internal threaded drive element 130, to be constructed of metal or another high-strength material. In some cases, it may be acceptable to have a radio-opaque strut, and solid or thick-walled metal elements can be used. In other cases where a reduced level of x-ray absorption is desired, the strut elements 100, 130, and 200, 300 can be fabricated in the form of thin-walled tubes (i.e., less than 1 mm thick) in order to reduce weight and x-ray absorption. Accordingly, structures described herein can be made from metals and other radio-opaque materials, as well as from radiolucent materials, for example.

Figure 6:
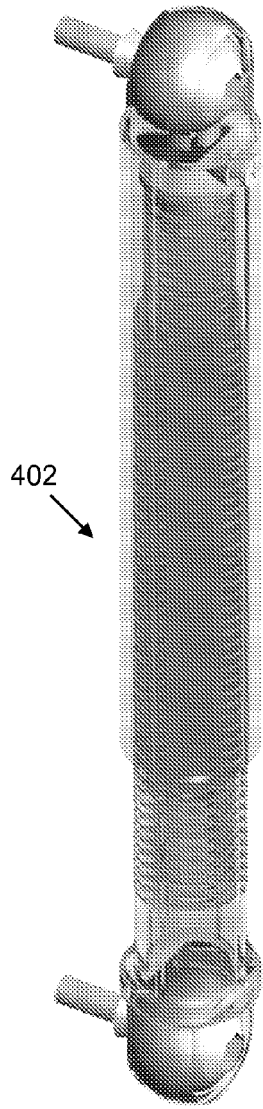
FIG. 6 is a perspective view of an optically translucent version of a strut of the invention.

In some other orthopaedic applications, the maximum load-carrying strength of a strut may be low enough that the strut elements can be made of reinforced polymer materials. In other orthopaedic applications, the maximum load carrying capacity of a strut may be low enough that the major strut elements can be made of a strong but unfilled polymer such as polycarbonate. FIG. 6 shows an embodiment of the invention that is constructed of color-tinted polycarbonate 402. Of course, the tinting can be removed if it desired to choose an optically clear polycarbonate (not shown). Such optically clear and/or color tinted struts provide a less intimidating and imposing visual appearance, and thus may be judged to be more attractive by patients who will be "wearing" an external fixation frame for months at a time.

Figure 7:
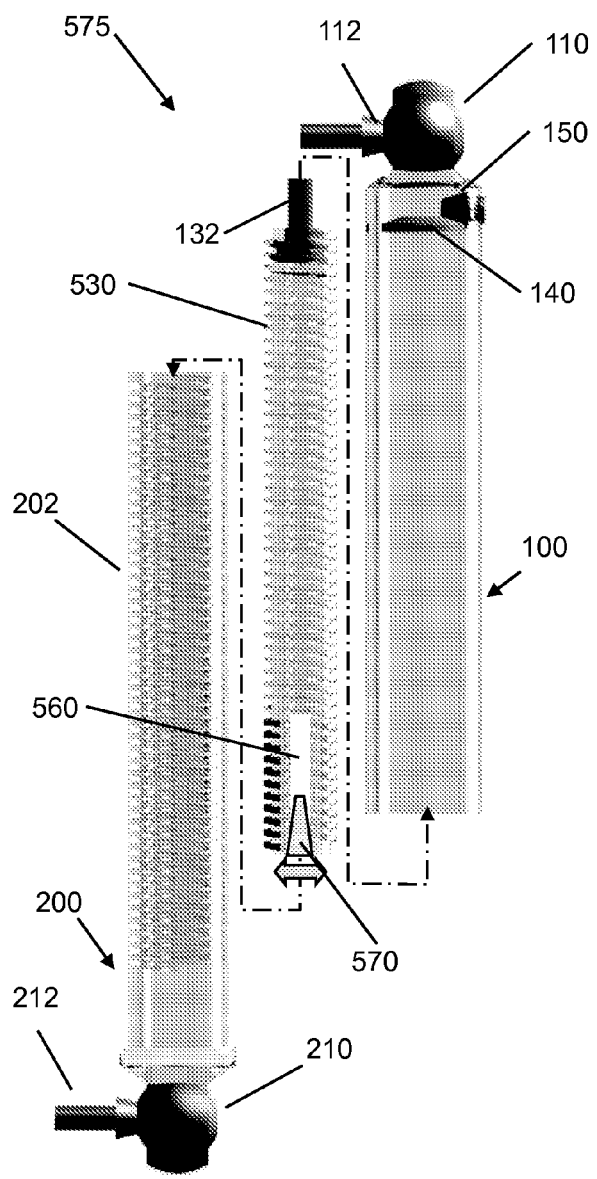
FIG. 7 is an exploded view of an embodiment of the present invention illustrating preloading for elimination of backlash.

It is important that the strut assembly can precisely hold a defined total length without excessive clearances and associated mechanical backlash, which limits mechanical positioning accuracy and stiffness. FIG. 7 illustrates an exploded view of a self-preloaded strut embodiment 575, which reduces or eliminates axial backlash. In this embodiment, the hollow threaded drive element 130 in FIG. 3 has been modified to a threaded drive element 530, such that a portion of the threaded region has been cut along at least one radial line. This is illustrated in FIG. 7 where threaded drive element 530 contains one or more axial slots 560 at one end. A compliant preload plug 570 inserted into the open end of the hollow and slotted drive element 530 acts to radially expand a portion of the threads near the end of the drive element 530. When the threaded drive element 530 is then threaded inside the inner telescoping strut element 200, the preload plug 570 acts to expand the threads of the drive element 530 until they are in intimate contact with the threads 202 (shown most clearly on FIG. 3) on the inner telescoping strut 200. If the threads have an angled profile, as is commonly used for example, the elimination of the radial clearance also results in the elimination of axial thread clearance, and the axial backlash in the threaded connection is thus eliminated or substantially eliminated. It will also be apparent to those skilled in the art that, without departing from the scope of the invention, the thread clearance could also be removed by radially compressing a portion of the outer threaded element, instead of radially expanding a portion of the inner threaded element. It will also be apparent to those skilled in the art that other methods can be employed for producing the desired preload, including but not limited to, the use of springs of any type, pressurized bladders, or the intentional interference fit between the parts, without departing from the scope of the invention.

If pivoting joints such as rod-ends 110 and 210 are required, they can also be preloaded to remove axial backlash using compliant plugs, springs, material interference, or other common design techniques to minimize or eliminate clearance between the rod-end post elements 112 and 212 and the body of the inner and outer telescoping strut elements, 100 and 200 respectively. It will be apparent to those skilled in the art that other detailed forms of preloading or backlash elimination can be used to remove the clearance between the threaded drive element 130, 530 and both the inner telescoping strut element 200 and the outer telescoping strut element 100 without departing from the scope of the invention.

FIG. 8 illustrates a section view of an assembled, fully preloaded embodiment of a strut assembly 575. Axial pre-loading of the threaded connection between the inner telescoping strut element 200 and the threaded drive element 530 is created by the compliant plug 570 which acts to radially expand a region of threads on threaded drive element 530, which may have a slot 560 to reduce the circumferential stiffness of the end of the threaded drive element 530. Because there is a risk that the slotted portion 560 of the threaded drive element 530 could crack under large loads, it is preferred to have both a preloaded section and an un-preloaded section of threads on drive element 530 which engage with threads on inner telescoping strut element 200, so that the un-preloaded thread section will still be available to maintain axial position (albeit with some backlash) if for some reason the preloaded section of threads were to fail.

FIG. 8 also illustrates the use of a wavy washer 134, or other compliant element, placed under the head of shoulder screw 132 which rotatably connects the threaded drive element 530 (together with the affixed bevel gear 140) to the end portion of the outer telescoping strut element 100. The wavy washer 134 acts to preload the threaded drive element 530 (and affixed bevel gear 140) against the outer telescoping strut element 100, and thus eliminates any free backlash resulting from clearances and tolerances in the length of the shoulder on shoulder screw 132. If a compliant element such as a wavy washer is used with the shoulder screw 132 which rotatably mounts the threaded drive element 530 to the outer telescoping strut element 100, then the axial "free play" or backlash of that joint is also eliminated.

When preloading an axial device in this manner, the clearance is removed by forcing one element towards the other with some amount of preload force. If the elements are pushed in one direction, they will already be in intimate contact and the stiffness of the system is defined by the material properties and the stiffness of the material-to-material contact at the joint. If the elements are pushed in the opposite direction, any motion is initially prevented by the preload force. If, however, the applied force is larger than the preload force, the elements will move axially relative to one another. Thus, it can be seen that axial preloading is asymmetric. If the strut is to be used primarily to resist large compressive forces (i.e., forces acting to shorten the strut) then the wavy washer or other compliant element should be placed underneath the head of the shoulder screw 132 which is placed inside of the hollow threaded drive element 530. This ensures that the threaded drive element 530 is held in intimate contact with the solid end portion of the outer telescoping element 100 and there will be no axial backlash even under large compressive loads. If, on the other hand, the strut is to be used primarily to resist tensile forces (those acting to lengthen the strut), then the wavy washer should be placed over the threaded shoulder screw 132 in the region between the bevel gear 140 and the end of the outer telescoping strut element 100.

FIG. 8 also illustrates the use of compliant elements 118 and 218 in the cavities of the rod-end joints, to preload any internal stud or other mating element (such as 112 and 212 shown on FIG. 7) which would be fitted inside the rod-end cavities.

FIG. 9 illustrates a further embodiment of a strut assembly 675, wherein the lower spherical rod-end is held in place by a stack of rigid and elastic elements, comprising solid elements 610 and 612 interleaved with elastic elements 620 and 622, and with the entire stack fitted inside inner telescoping strut element 200. Also shown are two tapered pins 630 and 632, which can be engaged to lock the rigid elements 610 and 612 into position relative to the telescoping element 200. When pin 630 is engaged, the system has maximum stiffness because rigid element 610 blocks the (upward) motion of the lower spherical rod end. If pin 630 is not present while pin 632 is inserted, however, the strut has an intermediate stiffness in the strut-shortening direction because the elastic element 620 sandwiched between solid elements 610 and 612 can compress under load. Furthermore, if both pins 630 and 632 are removed or otherwise disengaged, the system will have further reduced stiffness because both compliant elements 620 and 622 can compress under load. Of course, the number and thickness of compliant elements and locking pins can be changed to provide additional stiffness options. It will be understood by those skilled in the art that disengagement of a locking pin may be achieved by complete removal of the pin, partial removal or other shift in the position of the pin, rotation of a flattened or other non-round pin, or by other means.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

We claim:

1. An adjustable length strut apparatus for orthopaedic applications comprising:
   a first strut element with a first end joint;
   a second strut element with a second end joint;
   a threaded drive element for adjusting the relative position of the first strut element relative to the second strut element;
   at least one compliant element which is compressed when one end joint is moved towards the other end joint; and
   at least one disengageable locking pin that substantially prevents compression of the at least one compliant element when the disengageable locking pin is engaged.

2. An adjustable length strut apparatus as claimed in claim 1, wherein the at least one compliant element comprises an alternating stack of rigid and compliant sub-elements.

3. An adjustable length strut apparatus as claimed in claim 1, further comprising a plurality of disengageable locking pins, and wherein sequential disengagement of the disengageable locking pins produces a sequential reduction in the stiffness of the adjustable length strut apparatus.

* * * * *